US00PP14557P29

(12) United States Plant Patent
Kataoka

(10) Patent No.: US PP14,557 P2
(45) Date of Patent: Feb. 24, 2004

(54) *GAURA LINDHEIMERI* PLANT NAMED 'MY MELODY'

(50) Latin Name: *Gaura lindheimeri*
Varietal Denomination: My Melody

(75) Inventor: Michio Kataoka, Niitsu (JP)

(73) Assignee: Nichien Co., Ltd., Niigata (JP)

( * ) Notice: Subject to any disclaimer, the term of this patent is extended or adjusted under 35 U.S.C. 154(b) by 0 days.

(21) Appl. No.: 10/287,356

(22) Filed: Nov. 4, 2002

(51) Int. Cl.[7] ..... A01H 5/00
(52) U.S. Cl. ..... Plt./226
(58) Field of Search ..... Plt./226

*Primary Examiner*—Kent Bell
*Assistant Examiner*—Louanne Krawczewicz Myers
(74) *Attorney, Agent, or Firm*—Webb Ziesenheim Logsdon Orkin & Hanson, P.C.

(57) ABSTRACT

A new and distinct *Gaura lindheimeri* plant with white flowers and a long blooming season.

3 Drawing Sheets

Botanical classification: *Gaura lindheimeri.*
Varietal denomination: 'My Melody'.

BACKGROUND OF THE INVENTION

The present invention comprises a new and distinct cultivar of *Gaura lindheimeri* known by the varietal name 'My Melody'. The new variety was discovered in Niigata, Japan. The variegated seedling was selected and confirmed as a stable selection on May 20, 1999 in Niigata, Japan. The new variety is the result of a planned breeding program between *Gaura lindheimeri* (short-form) (female unpatented, unnamed parent) and *Gaura lindheimeri* (male unpatented, unnamed parent). The new variety exhibits similar large white flowers to both parents, but has a variegated foliage. The new variety exhibits similar flower color to the unpatented variety 'Corries Gold', but has a more compact, free branching habit. The new variety was first asexually reproduced by cuttings in Niigata, Japan. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
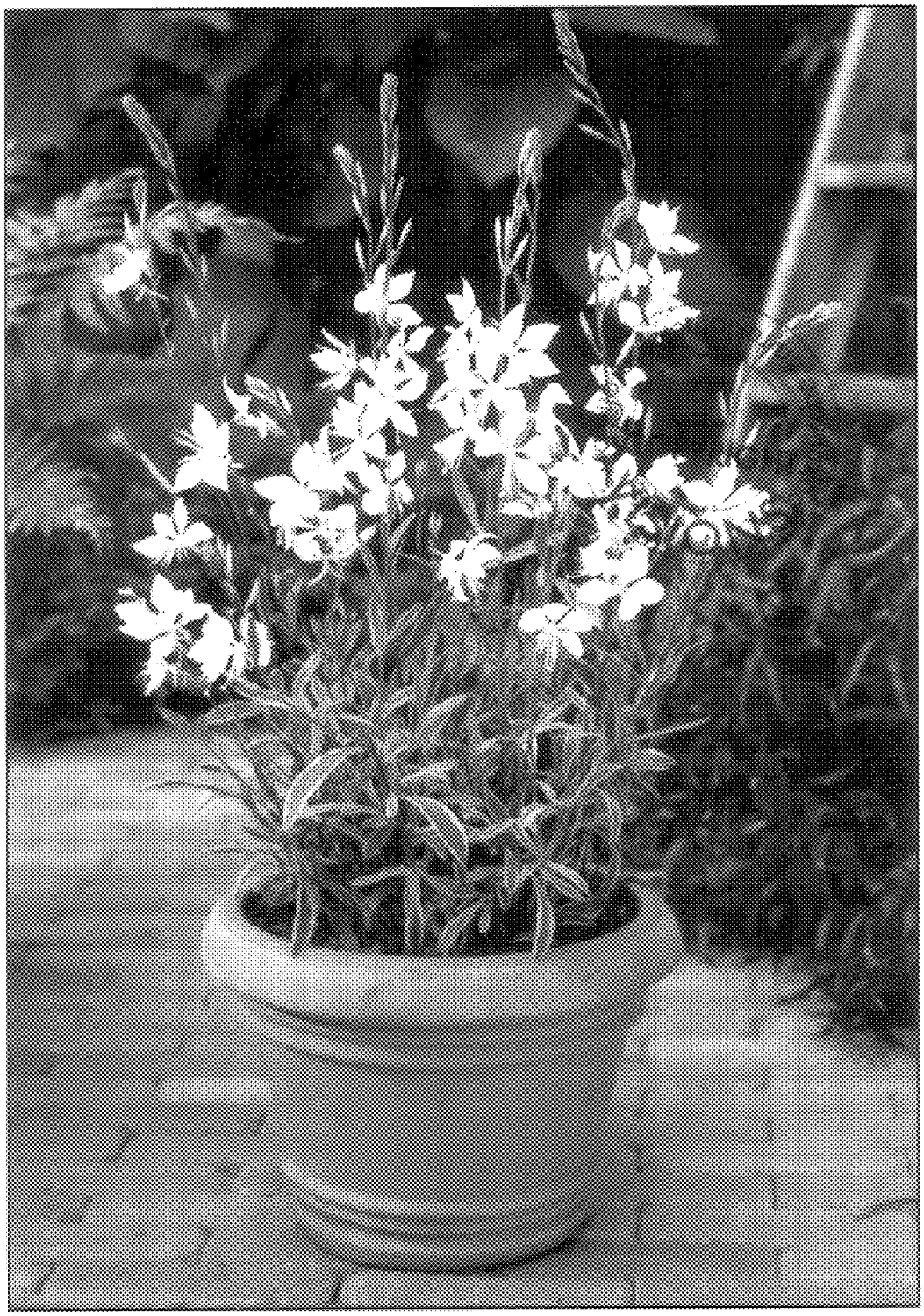
FIG. 1 is a photograph of the new plant.
Figure 2:
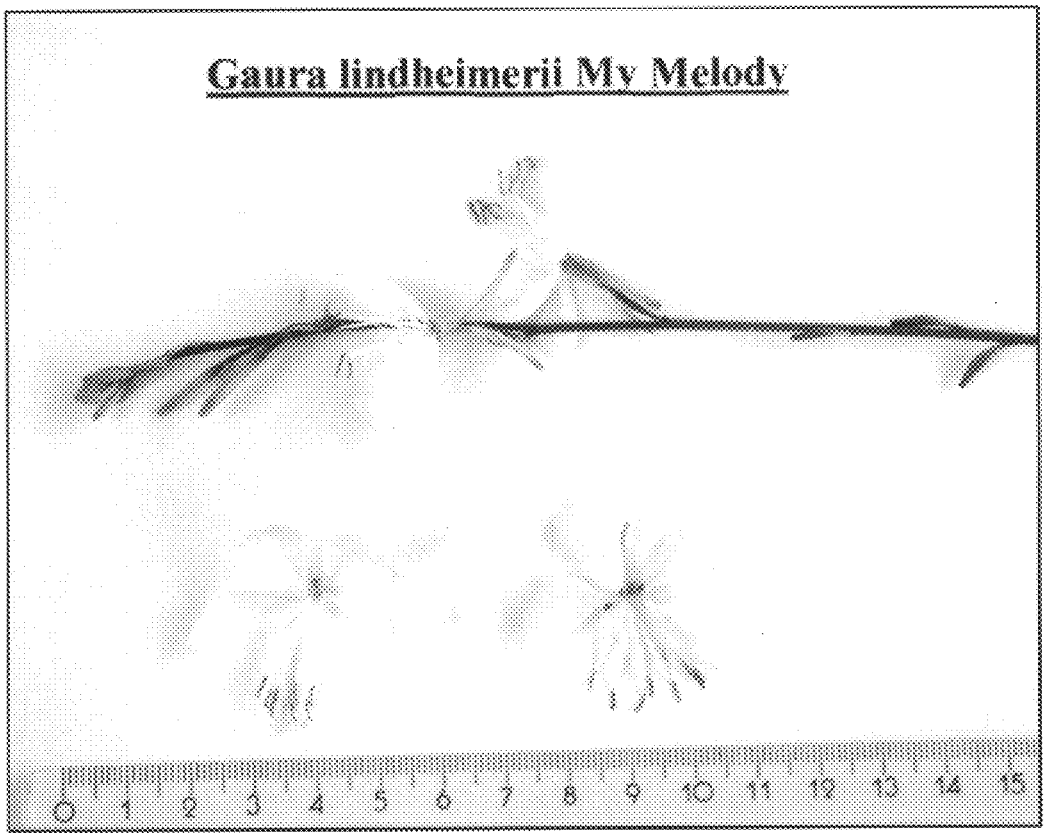
FIG. 2 is a photograph of the spike and flowers of the new plant.
Figure 3:
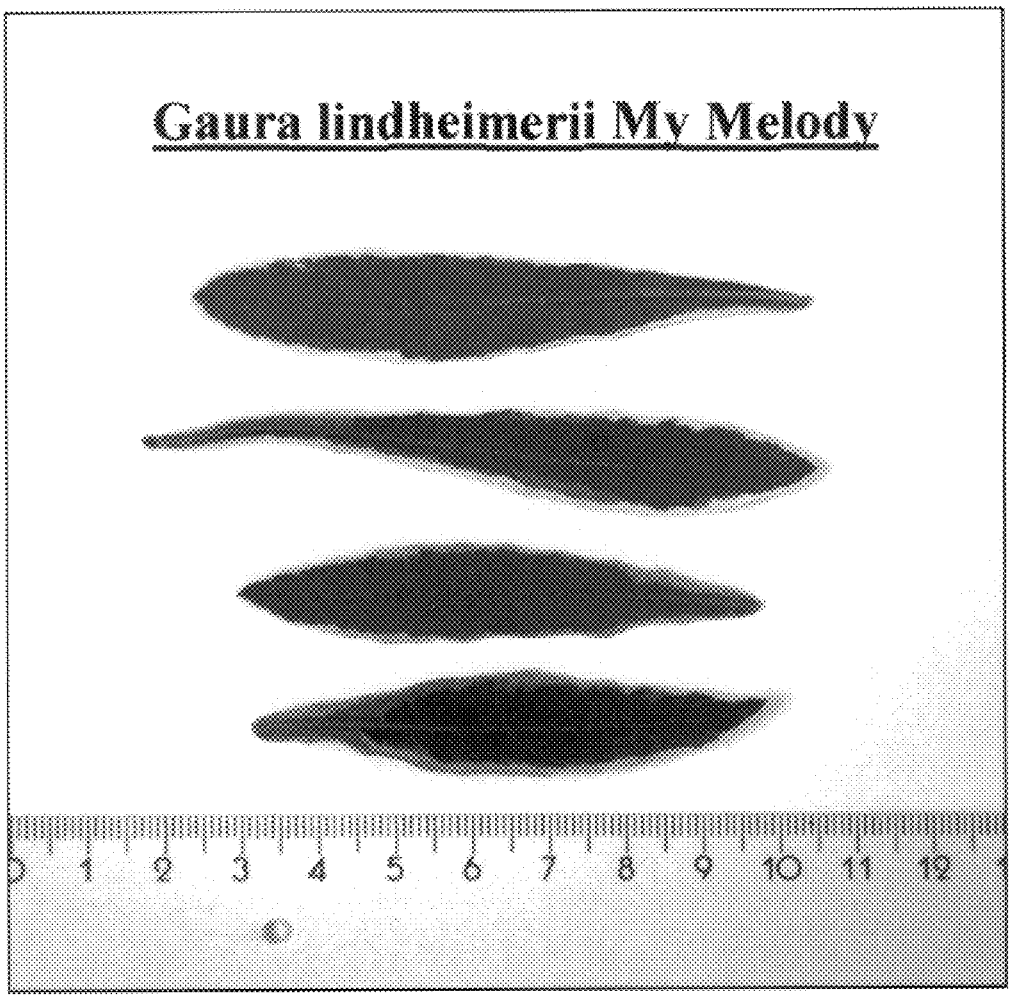
FIG. 3 is a photograph of the leaves of the new plant.

The following detailed description sets forth the characteristics of the new cultivar grown outside in the open ground and in 15 cm diameter containers with no extra fertilizer in The Netherlands. Plants were about 4 to 5 months old. The data which defines these characteristics were collected by asexual reproductions by cuttings. The color readings were taken in The Netherlands in natural daylight. Color references are primarily to The R.H.S. Colour Chart of The Royal Horticultural Society of London.

PLANT

Time to initiate roots: 10 days at 22° C.
Time to develop roots: 30 days at 18° C.
Time to produce a finished flowering plant from a rooted cutting: 7.5 weeks in a 9 cm container.
Form: Upright; slightly spreading.
Stem:
- *Length.*—45–50 cm.
- *Diameter.*—Average 4 mm.
- *Color.*—143C.
- *Texture.*—Smooth.
- *Pubescence.*—Light.
- *Form.*—Erect.

Height: In a pot, blooms are 40 cm above soil. In the ground, blooms are 60 cm above soil.
Diameter: 20 cm in a pot; 35 cm in the ground.
Vigor: Medium.
Branching habit: Free.
Lateral branches:
- *Length.*—About 20 cm.
- *Diameter.*—Average 2 mm.
- *Internode length.*—Average 16 mm, but irregular.
- *Texture.*—Smooth.
- *Pubescence.*—Light.
- *Color.*—137C.

Foliage:
- *Arrangement.*—Alternate.
- *Size of leaf.*—Length: About 6.8 cm. Width: About 1.0 cm.
- *Shape of leaf.*—Oblanceolate.
- *Shape of apex.*—Acute.
- *Shape of base.*—Attenuate.
- *Texture.*—Soft, slightly pubescent.
- *Margin type.*—Entire, slightly undulate.
- *Pubescence.*—Slight on upper and lower surfaces.

Color:
- *Young leaves.*—Upper surface: Center varies between 137C and 138A. Edge is 144C with 139D patches between the center and edge. Lower surface: Center is 137C. Edge is 144C with 139D patches between the center and edge.
- *Mature leaves.*—Upper surface: Center 137C. Edge is 4C with patches of 138B and 138C between the center and edge. Lower surface: Center is 138A.

Edge is 4C with patches of 138B and 138C between the center and edge.

Petiole: None present.

Veins:

*Color.*—Upper surface: 137C. Lower surface: 138A.

FLOWER

Bud:

*Stage when bud characteristics determined.*—Fully developed.

*Shape.*—Linear.

*Diameter.*—About 2.5 mm.

*Length.*—About 16 mm.

*Color.*—4D flushed with 39A and 39B.

Natural flowering season: In Northern Europe from May to November outside.

Spike:

*Number of flowers per spike.*—Average 27.

*Length.*—Average 25 cm.

Diameter across bloom: Average 6.5 cm.

Corolla:

*Form.*—Zygomorphic.

*Petals/lobes.*—Number: 4. Length: About 18 mm. Width: About 10 mm. Shape: Obovate. Apex: Rounded (obtuse). Base: Cuneate. Margin: Entire. Texture and appearance: Smooth, matte. Color: Upper surface: 155D. Lower surface: 155D.

Calyx:

*Form.*—Fused at tip.

*Length.*—About 16 mm.

*Diameter.*—About 5 mm.

*Sepal number.*—4(2 joined pairs).

*Sepal shape.*—Linear.

*Sepal margin: Entire.*

*Sepal texture.*—Smooth, pubescent.

*Sepal size.*—Length: About 16 mm. Width: About 2 mm.

*Sepal color.*—Upper surface: 155D flushed with 63B and 63C. Lower surface: 155D flushed with 63B and 63C.

*Pedicel.*—Length: 9 mm. Width: 1.5 mm. Color: 143C with lines of 59B.

*Peduncle.*—Length: 20–25 cm. Width: 1.5 mm. Color: 143A with 59A at tip of shoot.

Fragrance: None.

Disease resistance: Good.

Temperature tolerance: Good.

Drought tolerance: Good.

Lasting quality: Flowers last 1 day individually.

REPRODUCTIVE ORGANS

Stamens:

*Number.*—8 per flower.

*Filament length.*—About 14 mm.

*Anthers.*—Shape: Linear. Length: 3 mm. Color: 59A.

*Pollen.*—Color: Varies between 6C and 7C. Amount: Plentiful.

Pistils:

*Number.*—One.

*Length.*—27 mm.

*Style.*—Length: 26 mm. Color: 155A flushed with 63C and 63D.

*Stigma.*—Shape: Cruciform. Color: 3C.

I claim:

1. A new and distinct variety of *Gaura lindheimeri* plant substantially as shown and described.

* * * * *